United States Patent
Fukuda et al.

(10) Patent No.: US 6,784,306 B2
(45) Date of Patent: Aug. 31, 2004

(54) FLUORINATED ORGANOSILICON COMPOUNDS

(75) Inventors: Kenichi Fukuda, Gunma-ken (JP); Koichi Yamaguchi, Gunma-ken (JP)

(73) Assignee: Shin-etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/077,886

(22) Filed: Feb. 20, 2002

(65) Prior Publication Data

US 2002/0161115 A1 Oct. 31, 2002

(30) Foreign Application Priority Data

Feb. 20, 2001 (JP) ........................................ 2001-042717

(51) Int. Cl.$^7$ ............................... C07F 7/04; C07F 7/08
(52) U.S. Cl. ..................... 556/434; 556/431; 556/435; 556/443; 556/444; 556/451; 556/454
(58) Field of Search ................................ 556/431, 434, 556/435, 443, 444, 451, 454; 528/31, 35, 36

(56) References Cited

U.S. PATENT DOCUMENTS

| 5,288,829 | A | * | 2/1994 | Takago et al. ................. 528/15 |
| 5,578,381 | A | * | 11/1996 | Hamada et al. .............. 428/447 |
| 6,500,976 | B2 | * | 12/2002 | Matsuda et al. ............. 556/431 |

FOREIGN PATENT DOCUMENTS

| EP | 0 435 654 A1 | 7/1991 |
| JP | 3-197484 | 8/1991 |

* cited by examiner

*Primary Examiner*—Jeffrey B. Robertson
(74) *Attorney, Agent, or Firm*—Birch, Stewart, Kolasch & Birch, LLP

(57) ABSTRACT

Fluorinated organosilicon compounds having at least one fluorinated organic group and at least three SiH groups in a molecule are capable of hydrosilylation reaction with such compounds as vinyl group-bearing fluoro-polymers in a stable manner and fully compatible therewith.

10 Claims, 1 Drawing Sheet

FLUORINATED ORGANOSILICON COMPOUNDS

This invention relates to novel fluorinated organosilicon compounds useful as a crosslinking agent for addition reaction.

BACKGROUND OF THE INVENTION

Rubber compositions of the addition reaction curing type generally contain a base polymer having alkenyl groups such as vinyl groups, a compound having hydrogen atoms directly attached to silicon atoms (i.e., SiH groups), and an addition reaction catalyst such as a platinum group catalyst. Cure takes place through the addition of the SiH groups to the alkenyl groups on the base polymer.

Organosilicon compounds having SiH groups are known in the art. For example, JP-A 3-197484 discloses an organosilicon compound of the structure that a SiH group is attached to a silicon atom having a fluoroalkyl substituent through an oxygen atom, as shown by the following formula.

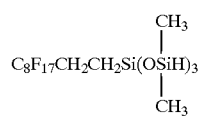

This compound is capable of hydrosilylation reaction with vinyl group-bearing compounds, and it is a useful raw material from which various derivatives are synthesized. For example, modifiers, crosslinking agents for resins and rubber, surfactants, and additives can be synthesized from this compound.

However, the use of this compound as a crosslinking agent gives rise to the problem that the compound is likely to volatilize upon curing at elevated temperatures so that cured properties become unstable.

A compound of the following formula is also known.

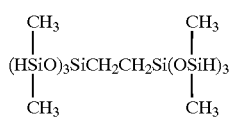

When this compound is used as a crosslinking agent in a composition comprising as a base polymer a polymer having a high fluorine content such as perfluoropolyether, the composition lacks storage stability and cure stability because of poor compatibility between the components.

SUMMARY OF THE INVENTION

An object of the invention is to provide a novel fluorinated organosilicon compound having SiH groups capable of hydrosilylation reaction with such compounds as vinyl group-bearing fluoro-polymers in a stable manner and fully compatible therewith.

We have found that a fluorinated organosilicon compound having at least one fluorinated organic group and at least three SiH groups in a molecule as shown by the general formula (1) below is capable of hydrosilylation reaction with such compounds as vinyl group-bearing fluoro-polymers in a stable manner and is fully compatible with such polymers.

The invention provides a fluorinated organosilicon compound having the following general formula (1).

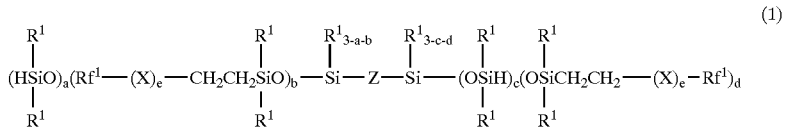

Herein $R^1$ is independently a monovalent hydrocarbon group having 1 to 6 carbon atoms; X is independently $-CH_2-$, $-CH_2O-$, $-CH_2OCH_2-$ or $-Y-NR^2-CO-$ wherein Y is $-CH_2-$ or a divalent group of the following structural formula (I):

and $R^2$ is hydrogen or a monovalent hydrocarbon group having 1 to 10 carbon atoms; $Rf^1$ is a monovalent perfluoroalkyl or perfluorooxyalkyl group; Z is a divalent hydrocarbon group of 1 to 15 carbon atoms which may contain an ether bond; subscripts a, b, c and d are integers satisfying $a \leq 3$, $b \leq 3$, $c \leq 3$, $d \leq 3$, $3 \leq a+c \leq 5$, $1 \leq b+d \leq 3$, $a+b \leq 3$, and $c+d \leq 3$, and e is independently 0 or 1.

DESCRIPTION OF THE PREFERRED EMBODIMENT

Figure 1:
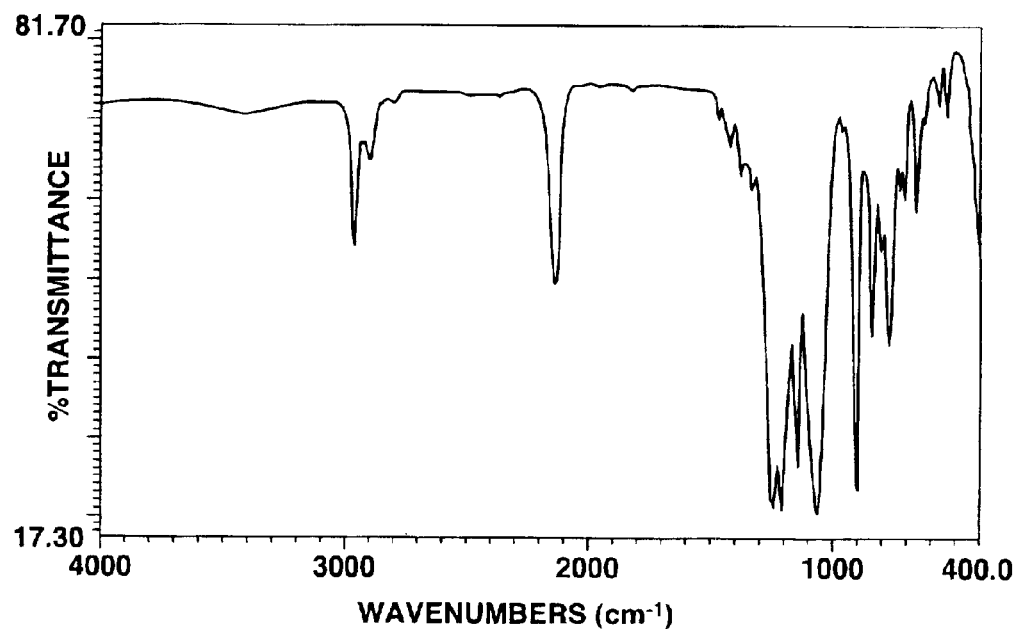
FIG. 1 is a diagram showing an IR absorption spectrum of the compound synthesized in Example 1.

The fluorinated organosilicon compound of the invention has at least one fluorinated organic group and at least three SiH groups in a molecule as shown by the general formula (1) below.

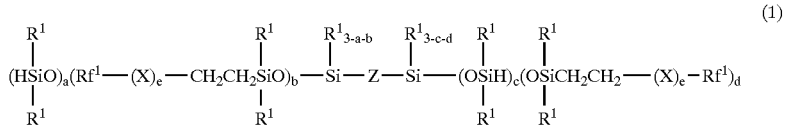

Herein X is independently —CH$_2$—, —CH$_2$O—, —CH$_2$OCH$_2$— or —Y—NR$^2$—CO— wherein Y is —CH$_2$— or a divalent group of the following structural formula (I).

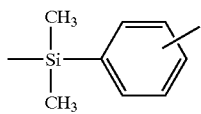

R$^2$ is hydrogen or a monovalent hydrocarbon group having 1 to 10 carbon atoms, preferably 1 to 6 carbon atoms.

The monovalent hydrocarbon groups represented by R$^2$ include unsubstituted monovalent hydrocarbon groups, for example, alkyl groups such as methyl, ethyl, propyl, butyl, hexyl, cyclohexyl and octyl, cycloalkyl groups, aryl groups such as phenyl and tolyl, and aralkyl groups such as benzyl and phenylethyl, and substituted monovalent hydrocarbon groups obtained by replacing some or all of the hydrogen atoms in the foregoing groups by halogen atoms such as fluorine.

Rf$^1$ is a monovalent perfluoroalkyl or perfluorooxyalkyl group. The preferred monovalent perfluoroalkyl groups are of the formula: —C$_h$F$_{2h+1}$ wherein h is an integer of 1 to 20, preferably 2 to 16.

The monovalent perfluorooxyalkyl groups are preferably those of 1 to 500 carbon atoms, especially 1 to 300 carbon atoms. Preferred examples are given below.

Z is a divalent hydrocarbon group of 1 to 15 carbon atoms, preferably 1 to 12 carbon atoms, more preferably 1 to 10 carbon atoms, which may contain an ether bond (—O—). Examples include alkylene groups such as methylene, ethylene, propylene, methylethylene, butylene and hexamethylene, cycloalkylene groups such as cyclohexylene, and arylene groups such as phenylene, tolylene, xylylene, naphthylene and biphenylene, and combinations of any. Another example of Z is a divalent group containing an oxygen atom in the foregoing backbone structure. Herein the oxygen atom intervenes in the form of —O—.

R$^1$ which may be the same or different is a monovalent hydrocarbon group having 1 to 6 carbon atoms. Illustrative are alkyl groups such as methyl, ethyl, propyl, isopropyl, butyl, isobutyl, tert-butyl, pentyl, neopentyl and hexyl, alkenyl groups such as vinyl and allyl, and aryl groups such as phenyl. Of these, methyl and phenyl are especially preferred.

The subscripts a, b, c and d are integers satisfying a≦3, b≦3, c≦3, d≦3, 3≦a+c≦5, 1≦b+d≦3, a+b≦3, and c+d≦3, so that the compound of the invention has at least one fluorinated organic group and at least three SiH groups in a molecule.

The subscript e is independently equal to 0 or 1.

Preferably, the fluorinated organosilicon compounds have the following general formula (2).

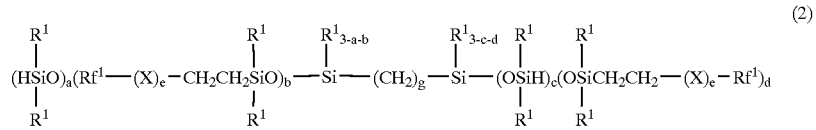

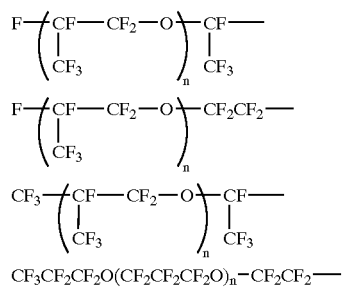

(n is an integer of 1 to 100.)

Herein R$^1$, X, Rf$^1$, a, b, c, d and e are as defined above and g is an integer of 1 to 8, preferably 1 to 4.

Several exemplary fluorinated organosilicon compounds are given below, but the fluorinated organosilicon compounds of the invention are not limited thereto. Note that Me is methyl and Ph is phenyl.

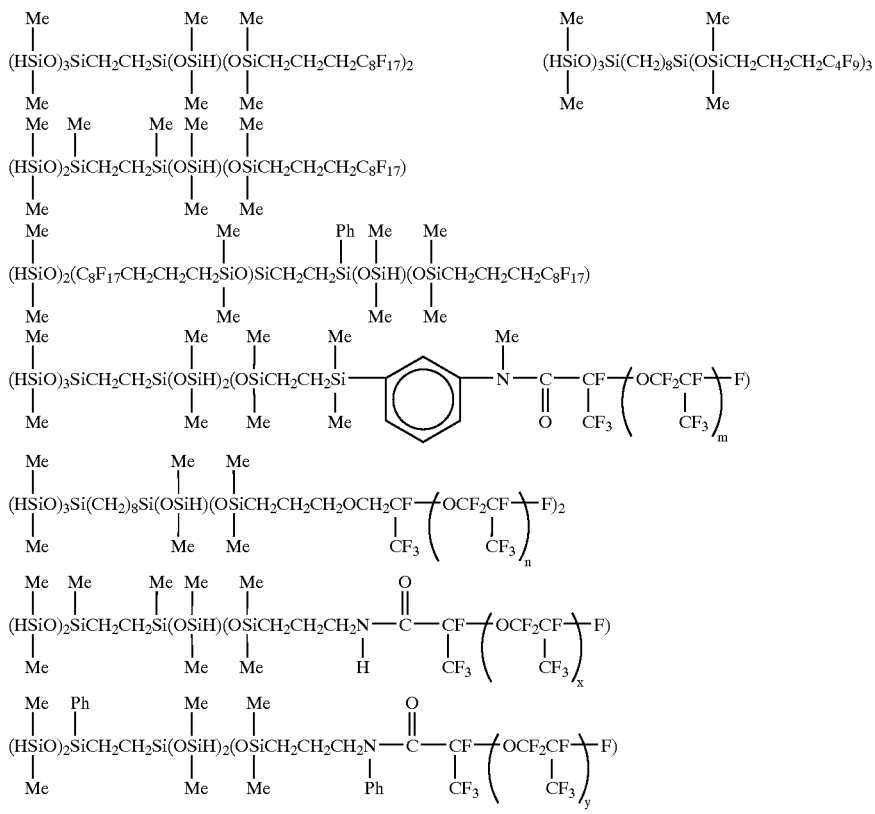

m = 1 to 100
n = 1 to 100
x = 1 to 100
y = 1 to 100

The fluorinated organosilicon compound of formula (1) can be synthesized, for example, by effecting addition reaction of an alkenyl group-containing fluorine compound of the following general formula (4) to a polyfunctional SiH compound of the following general formula (3).

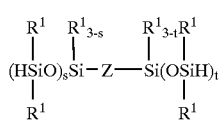
(3)

Herein s is an integer of 1 to 3, t is an integer of 1 to 3, s+t is from 4 to 6, Z and $R^1$ are as defined above.

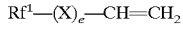
(4)

Herein $Rf^1$, X and e are as defined above.

Specifically, the compound of formula (2) can be obtained by effecting addition reaction of an alkenyl group-containing fluorine compound of formula (4) to a polyfunctional SiH compound of the following general formula (5) in the presence of an addition reaction catalyst such as a platinum compound.

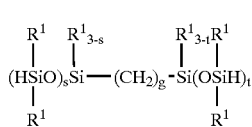
(5)

Herein, $R^1$, s, t and g are as defined above.

Shown below is the reaction scheme in the event where a polyfunctional SiH compound of formula (5) wherein s=t=3 is used.

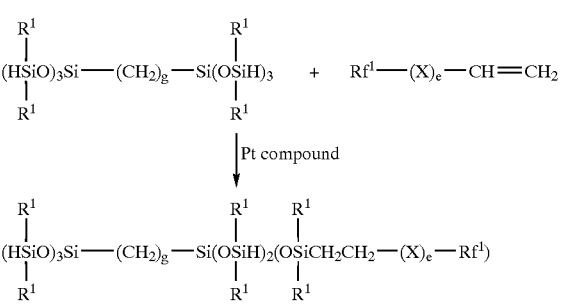

Herein, $R^1$, $Rf^1$, X, s, t, g and e are as defined above.

The synthesis of the compound of formula (1) can be carried out by the method and conditions known for addition reaction or hydrosilylation. A solvent may be used for reaction to take place. The preferred solvent is toluene, xylene, bistrifluorobenzene or the like. The amount of the compound of formula (4) added to the compound of formula (3) or (5) is determined such that a, b, c and d in formula (1) or (2) fall in the above-defined range.

The fluorinated organosilicon compound of the invention can be utilized not only as a crosslinking agent for addition reaction, but also as an intermediate for modification and in various other applications.

EXAMPLE

Examples of the invention are given below by way of illustration and not by way of limitation.

Example 1

A 1-liter four-necked flask equipped with a stirrer, thermometer, condenser and dropping funnel was charged with 370 g of a compound of the following formula (6) and 200 g of toluene and heated at 80° C. Thereafter, 0.1 g of a toluene solution of chloroplatinic acid-vinylsiloxane complex (platinum concentration 0.5% by weight) was added, and 700 g of a compound of the following formula (7) added dropwise from the dropping funnel.

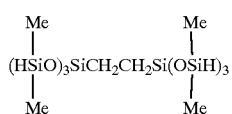

(6)

$C_8F_{17}CH_2CH=CH_2$ (7)

After the completion of dropwise addition, the reaction solution was aged at 80° C. for one hour. After the consumption of compound (7) was confirmed by gas chromatography, the reaction solution was cooled down.

Thereafter, 10 g of activated carbon was added to the reaction solution, which was stirred for one hour and filtered. The filtrate was stripped of the solvent under conditions of 120° C. and 3 Torr, yielding 990 g of a colorless clear liquid having a viscosity of 28 cs, a specific gravity of 1.327 and a refractive index of 1.364.

On analysis by $^1$H-NMR, IR and elemental analysis, this liquid was identified to be a compound having an average structure of the following formula (i). FIG. 1 is a chart of IR analysis.

(i)

$^1$H-NMR

δ 0.09 (s, C—Si—C$\underline{H}_3$: 12H)

δ 0.16 (s, H—Si—C$\underline{H}_3$: 24H)

δ 0.6–1.3 (m, Si—C$\underline{H}_2$—: 8H)

δ 1.5–2.3 (m, Si—CH$_2$—C$\underline{H}_2$—C$\underline{H}_2$—: 8H)

δ 4.72 (s, Si—$\underline{H}$: 4H)

IR 2130 cm$^{-1}$ $v_{Si—H}$

Elemental Analysis

|  | C | H | O | Si | F |
|---|---|---|---|---|---|
| Found (%) | 29.4 | 3.8 | 6.7 | 15.6 | 44.5 |
| Calcd. (%) | 29.7 | 3.9 | 6.6 | 15.4 | 44.4 |

Example 2

A 1-liter four-necked flask equipped with a stirrer, thermometer, condenser and dropping funnel was charged with 115 g of a compound of formula (6) and 100 g of bistrifluoromethylbenzene and heated at 80° C. Thereafter, 0.03 g of a toluene solution of chloroplatinic acid-vinylsiloxane complex (platinum concentration 0.5% by weight) was added, and 1850 g of a compound of the following formula (8) added dropwise from the dropping funnel.

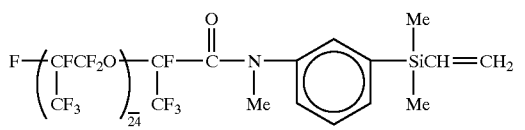

(8)

After the completion of dropwise addition, the reaction solution was aged at 80° C. for one hour and then cooled down.

Thereafter, 10 g of activated carbon was added to the reaction solution, which was stirred for one hour and filtered. The filtrate was stripped of the solvent under conditions of 120° C. and 3 Torr, yielding 1050 g of a colorless clear liquid having a viscosity of 2520 cs, a specific gravity of 1.709 and a refractive index of 1.333.

Figure 2:
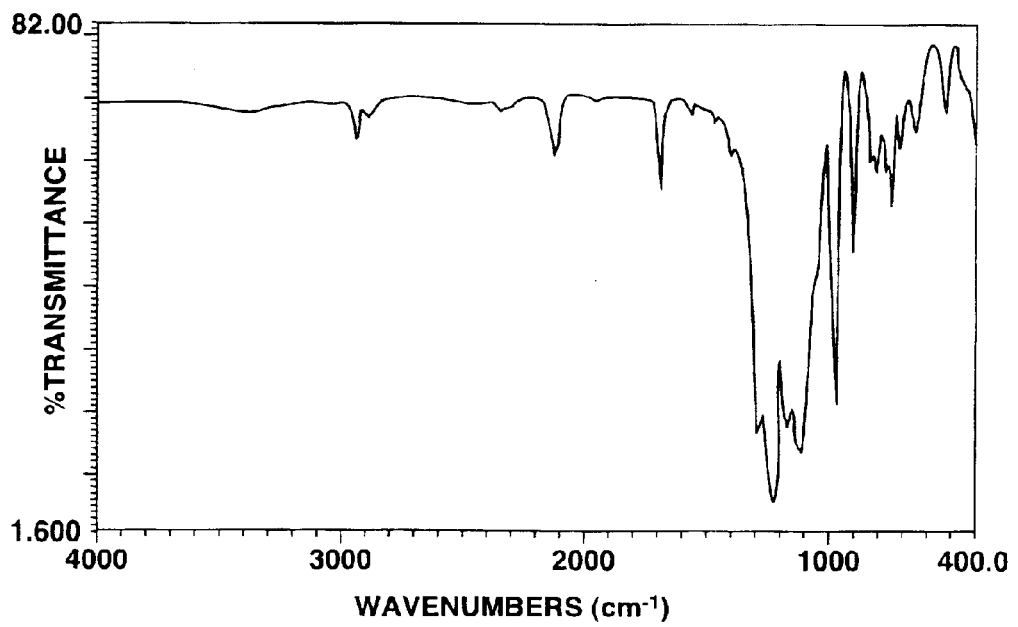
FIG. 2 is a diagram showing an IR absorption spectrum of the compound synthesized in Example 2.

On analysis by $^1$H-NMR, IR and elemental analysis, this liquid was identified to be a compound having an average structure of the following formula (ii). FIG. 2 is a chart of IR analysis.

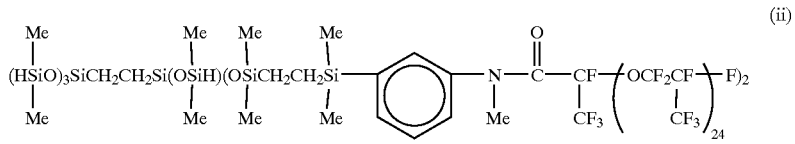

(ii)

¹H-NMR

δ 0.09 (s, C—Si—C$\underline{H_3}$: 6H)

δ 0.16 (s, H—Si—C$\underline{H_3}$: 30H)

δ 0.31 (s, arom. Si—C$\underline{H_3}$: 6H)

δ 0.6–1.3 (m, Si—C$\underline{H_2}$: 8H)

δ 3.23 (s, N—C$\underline{H_3}$: 3H)

δ 4.72 (s, Si—$\underline{H}$: 5H)

δ 7.2–7.7 (m, arom.: 4H)

IR 2130 cm$^{-1}$ $\nu_{Si-H}$

Elemental Analysis

|  | C | H | O | Si | F | N |
|---|---|---|---|---|---|---|
| Found (%) | 24.9 | 1.4 | 10.3 | 5.1 | 58.0 | 0.3 |
| Calcd. (%) | 24.7 | 1.3 | 10.2 | 5.2 | 58.3 | 0.3 |

There have been described fluorinated organosilicon compounds having SiH groups capable of hydrosilylation reaction with such compounds as vinyl group-bearing fluoropolymers in a stable manner and fully compatible therewith.

Japanese Patent Application No. 2001-042717 is incorporated herein by reference.

Reasonable modifications and variations are possible from the foregoing disclosure without departing from either the spirit or scope of the present invention as defined by the claims.

What is claimed is:

1. A fluorinated organosilicon compound having the following general formula (1):

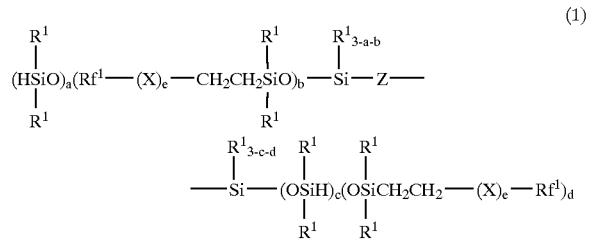

wherein $R^1$ is independently a monovalent hydrocarbon group having 1 to 6 carbon atoms, X is independently —$CH_2$, —$CH_2O$—, —$CH_2OCH_2$— or —Y—$NR^2$—CO— wherein Y is —$CH_2$— or a divalent group of the following structural formula (I):

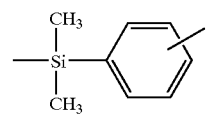

and $R^2$ is hydrogen or a monovalent hydrocarbon group having 1 to 10 carbon atoms, $Rf^1$ is a monovalent perfluoroalkyl or perfluorooxy-alkyl group, Z is a divalent hydrocarbon group of 1 to 15 carbon atoms which may contain an ether bond, subscripts a, b, c and d are integers satisfying a≦3, b≦3, c≦3, d≦3, 3≦a+c≦5, 1≦b+d≦3, a+b≦3, and c+d≦3, and e is independently 0 or 1.

2. The fluorinated organosilicon compound of claim 1 having the following general formula (2):

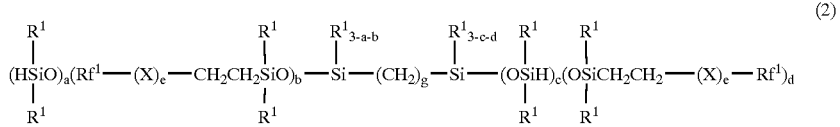

wherein $R^1$, X, $Rf^1$, a, b, c, d and e are as defined above and g is an integer of 1 to 8.

3. The fluorinated organosilicon compound of claim 1, wherein $R^2$ is a monovalent hydrocarbon group having 1 to 6 carbon atoms.

4. The fluorinated organosilicon compound of claim 1, wherein $R^2$ is selected from the group consisting of alkyl, cycloalkyl, aryl and aralkyl groups unsubstituted, or substituted by replacing some of all of the hydrogen atoms in the foregoing groups with halogen atoms.

5. The fluorinated organosilicon compound of claim 1, wherein $Rf^1$ is a perfluoroalkyl group of the formula —$C_hF_{2h+1}$ wherein h is an integer of 1 to 20.

6. The fluorinated organosilicon compound of claim 1, wherein $Rf^1$ is a perfluoroxyalkyl group of a formula selected from the group consisting of:

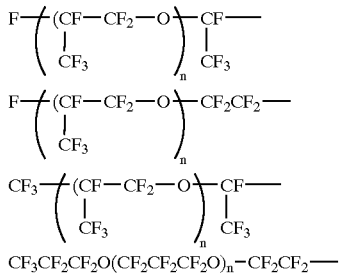

$$CF_3CF_2CF_2O(CF_2CF_2CF_2O)_n-CF_2CF_2-$$

wherein n is an integer of 1 to 100.

7. The fluorinated organosilicon compound of claim 1, wherein Z is divalent hydrocarbon group of 1 to 10 carbon atoms selected from the group consisting of alkylene, cycloalkyl and arylene groups which may optionally contain an ether bond.

8. The fluorinated organosilicon compound of claim 1, wherein $R^1$ is selected from the group consisting of alkyl, alkenyl and aryl groups.

9. The fluorinated organosilicon compound of claim 1, wherein $R^1$ is methyl or phenyl.

10. The fluorinated organosilicon compound of claim 2, wherein g is an integer of 1 to 4.

* * * * *